(12) United States Patent
Hlavka et al.

(10) Patent No.: US 9,089,700 B2
(45) Date of Patent: Jul. 28, 2015

(54) SYSTEMS AND METHODS FOR TREATING DYSPNEA, INCLUDING VIA ELECTRICAL AFFERENT SIGNAL BLOCKING

(75) Inventors: Edwin J. Hlavka, Minneapolis, MN (US); Lynn S. Elliott, Maple Grove, MN (US)

(73) Assignee: CIBIEM, INC., Los Altos, CA (US)

(*) Notice: Subject to any disclaimer, the term of this patent is extended or adjusted under 35 U.S.C. 154(b) by 722 days.

(21) Appl. No.: 12/537,984

(22) Filed: Aug. 7, 2009

(65) Prior Publication Data

US 2010/0070004 A1   Mar. 18, 2010

Related U.S. Application Data

(60) Provisional application No. 61/087,945, filed on Aug. 11, 2008.

(51) Int. Cl.
*A61N 1/34* (2006.01)
*A61N 1/36* (2006.01)
*A61N 1/05* (2006.01)

(52) U.S. Cl.
CPC ............ *A61N 1/3601* (2013.01); *A61N 1/0556* (2013.01)

(58) Field of Classification Search
CPC .... A61B 5/04; A61B 5/04001; A61B 5/7264; A61N 1/3601; A61N 1/36114; A61N 1/0556
USPC .......................................................... 607/42
See application file for complete search history.

(56) References Cited

U.S. PATENT DOCUMENTS

| | | | |
|---|---|---|---|
| 3,650,277 A | 3/1972 | Sjostrand et al. |
| 4,201,219 A | 5/1980 | Bozal |
| 4,791,931 A | 12/1988 | Slate |
| 4,960,133 A | 10/1990 | Hewson |
| 5,916,213 A | 6/1999 | Haissaguerre et al. |
| 5,919,187 A | 7/1999 | Guglielmi et al. |
| 6,068,629 A | 5/2000 | Haissaguerre et al. |
| 6,071,279 A | 6/2000 | Whayne et al. |

(Continued)

FOREIGN PATENT DOCUMENTS

| CN | 1440256 A | 9/2003 |
|---|---|---|
| DE | 10151797 A1 | 5/2003 |

(Continued)

OTHER PUBLICATIONS

Banzett, R.; Moosavi, S.; "Dyspnea and Pain: Similarities and Contrasts Between Two Very Unpleasant Sensations," APS Bulletin; vol. 11, No. 1; Mar./Apr. 2001.

(Continued)

*Primary Examiner* — Amanda Patton
(74) *Attorney, Agent, or Firm* — Shay Glenn LLP (57) ABSTRACT

Systems and methods for treating a patient with dyspnea are disclosed. A method in accordance with a particular embodiment includes identifying the patient as suffering from dyspnea, and, based at least in part on identifying the patient as suffering from dyspnea, implanting an electrical signal delivery element within the patient in signal communication with an afferent neural pathway of a carotid body chemoreceptor. The method can further include at least reducing dyspneic sensations in the patient by directing an electrical signal from the electrical signal delivery element to the neural pathway to at least partially block afferent signals from the chemoreceptor.

3 Claims, 5 Drawing Sheets

(56) References Cited

U.S. PATENT DOCUMENTS

| | | | |
|---|---|---|---|
| 6,125,857 A | 10/2000 | Silber | |
| 6,129,359 A | 10/2000 | Haas et al. | |
| 6,182,666 B1 | 2/2001 | Dobak, III | |
| 6,217,576 B1 | 4/2001 | Tu et al. | |
| 6,228,082 B1 | 5/2001 | Baker et al. | |
| 6,235,024 B1 | 5/2001 | Tu | |
| 6,402,746 B1 | 6/2002 | Whayne et al. | |
| 6,411,852 B1 | 6/2002 | Danek et al. | |
| 6,497,705 B2 | 12/2002 | Comben | |
| 6,522,926 B1 | 2/2003 | Kieval et al. | |
| 6,656,136 B1 | 12/2003 | Weng et al. | |
| 6,673,066 B2 | 1/2004 | Werneth | |
| 6,905,497 B2 | 6/2005 | Truckai et al. | |
| 6,937,903 B2 | 8/2005 | Schuler et al. | |
| 7,097,641 B1 | 8/2006 | Arless et al. | |
| 7,137,963 B2 | 11/2006 | Nita et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,207,989 B2 | 4/2007 | Pike et al. | |
| 7,363,076 B2 * | 4/2008 | Yun et al. | 607/3 |
| 7,617,005 B2 | 11/2009 | Demarais et al. | |
| 7,736,360 B2 | 6/2010 | Mody et al. | |
| 7,738,952 B2 | 6/2010 | Yun et al. | |
| 7,766,961 B2 | 8/2010 | Patel et al. | |
| 7,853,333 B2 | 12/2010 | Demarais | |
| 7,901,450 B2 | 3/2011 | Johnson et al. | |
| 7,922,663 B2 | 4/2011 | Tran et al. | |
| 7,925,352 B2 | 4/2011 | Stack et al. | |
| 7,959,628 B2 | 6/2011 | Schaer et al. | |
| 8,002,728 B2 | 8/2011 | Chang | |
| 8,060,206 B2 | 11/2011 | Kieval et al. | |
| 8,075,554 B2 | 12/2011 | Malecki et al. | |
| 8,116,883 B2 | 2/2012 | Williams et al. | |
| 8,157,760 B2 | 4/2012 | Criado et al. | |
| 8,167,805 B2 | 5/2012 | Emery et al. | |
| 8,192,760 B2 | 6/2012 | Hossainy et al. | |
| 8,292,879 B2 | 10/2012 | Manwaring et al. | |
| 8,308,709 B2 | 11/2012 | Chang | |
| 8,326,429 B2 | 12/2012 | Wenzel et al. | |
| 8,364,237 B2 | 1/2013 | Stone et al. | |
| 8,396,548 B2 | 3/2013 | Perry et al. | |
| 8,409,200 B2 | 4/2013 | Holcomb et al. | |
| 8,433,423 B2 | 4/2013 | Demarais | |
| 8,465,752 B2 | 6/2013 | Seward | |
| 2001/0041890 A1 | 11/2001 | Hassett et al. | |
| 2002/0087151 A1 | 7/2002 | Mody et al. | |
| 2003/0009125 A1 | 1/2003 | Nita et al. | |
| 2004/0116921 A1 | 6/2004 | Sherman et al. | |
| 2004/0210239 A1 | 10/2004 | Nash et al. | |
| 2005/0096710 A1 | 5/2005 | Kieval | |
| 2005/0143378 A1 | 6/2005 | Yun et al. | |
| 2005/0153885 A1 | 7/2005 | Yun et al. | |
| 2005/0288656 A1 | 12/2005 | Koerner et al. | |
| 2006/0064137 A1 | 3/2006 | Stone | |
| 2006/0195149 A1 | 8/2006 | Hopper et al. | |
| 2006/0224110 A1 | 10/2006 | Scott et al. | |
| 2006/0253161 A1 | 11/2006 | Libbus et al. | |
| 2006/0259084 A1 | 11/2006 | Zhang et al. | |
| 2006/0282131 A1 | 12/2006 | Caparso et al. | |
| 2006/0287679 A1 | 12/2006 | Stone | |
| 2007/0015006 A1 | 1/2007 | Lee et al. | |
| 2007/0112327 A1 | 5/2007 | Yun et al. | |
| 2007/0150006 A1 | 6/2007 | Libbus et al. | |
| 2007/0156179 A1 | 7/2007 | S.E. | |
| 2007/0299476 A1 | 12/2007 | Park et al. | |
| 2008/0009916 A1 | 1/2008 | Rossing et al. | |
| 2008/0009917 A1 | 1/2008 | Rossing et al. | |
| 2008/0045936 A1 | 2/2008 | Vaska et al. | |
| 2008/0058871 A1 | 3/2008 | Libbus et al. | |
| 2008/0086181 A1 | 4/2008 | Amurthur et al. | |
| 2010/0168731 A1 | 7/2010 | Wu et al. | |
| 2010/0268307 A1 | 10/2010 | Demarais et al. | |
| 2010/0274219 A1 | 10/2010 | Wenzel et al. | |
| 2011/0009854 A1 | 1/2011 | Babkin et al. | |
| 2011/0040297 A1 | 2/2011 | Babkin et al. | |
| 2011/0066085 A1 | 3/2011 | Weng et al. | |
| 2011/0098699 A1 | 4/2011 | Pachon et al. | |
| 2011/0104060 A1 | 5/2011 | Seward | |
| 2011/0130708 A1 | 6/2011 | Perry et al. | |
| 2011/0208096 A1 | 8/2011 | Demarais et al. | |
| 2012/0059437 A1 | 3/2012 | Shalev | |
| 2012/0078248 A1 | 3/2012 | Worrell et al. | |
| 2012/0172680 A1 | 7/2012 | Gelfand et al. | |
| 2012/0199616 A1 | 8/2012 | Lamb et al. | |
| 2013/0066316 A1 | 3/2013 | Steinke et al. | |
| 2013/0131668 A1 | 5/2013 | Schaer | |
| 2013/0197555 A1 | 8/2013 | Schaer | |
| 2013/0197614 A1 | 8/2013 | Gustus et al. | |
| 2014/0243809 A1 | 8/2014 | Gelfand et al. | |
| 2014/0350401 A1 | 11/2014 | Sinelnikov | |

FOREIGN PATENT DOCUMENTS

| | | |
|---|---|---|
| EP | 0819014 B1 | 2/2003 |
| EP | 1299035 B1 | 2/2013 |
| WO | WO-9843701 A1 | 10/1998 |
| WO | WO00/25685 A1 | 5/2000 |
| WO | WO03/076008 A1 | 9/2003 |
| WO | WO2004/105807 A2 | 12/2004 |
| WO | WO2007/092330 A1 | 8/2007 |
| WO | WO2007/146834 A2 | 12/2007 |
| WO | WO2008/025855 A2 | 3/2008 |
| WO | WO2010/093603 A1 | 8/2010 |
| WO | WO2010/124120 A1 | 10/2010 |
| WO | WO2010/132703 A1 | 11/2010 |

OTHER PUBLICATIONS

Handelsman, H.; "Bilateral Carotid Body Resection as a Treatment for Chronic Intractable Bronchospastic Diseases"; Health Technology Assessment Series: Health Technology Assessment Report; 1985; No. 12.

International Search Report No. PCT/US2009/053190; Applicant: Concept tx Medical, Inc.; Date of Mailing: Oct. 9, 2009 (2 pages).

O'Donnell, D.; "Pathophysiology of Dyspnea in Chronic Obstructive Pulmonary Disease"; Proceedings of the American Thoracic Society; 2007; p. 145-168; vol. 4.

Sedwitz, J. et al.; "Should the Carotid Body Be Removed in the Treatment of Asthma and Emphysema?"; International Surgery; Jun. 1972; p. 467-469; vol. 57, No. 6; Presented at the 7th European Federation Congress of the International College of Surgeons from Aug. 14-18; Hamburg.

Severinghaus, J.; "Carotid Body Resection for COPD?"; Chest; Jul. 31, 2008; p. 1128-1129; Issue 95; Northbrook, IL.

Somfay, A.; "Effect of Hyperoxia on Gas Exchange and Lactate Kinetics Following Exercise Onset in Nonhypoxemic COPD Patients"; Chest; Oct. 7, 2008; p. 393-400; Issue 121; Northbrook, IL.

Somfay, A. et al.; "Dose-Response Effect of Oxygen on Hyperinflation and Exercise Endurance in Non-Hypoxaemic COPD Patients"; European Respiratory Journal; 2001; p. 77-84; vol. 18; ERS Journals Ltd; UK.

Vermeire, P. et al.; "Carotid Body Resection in Patients With Severe Chronic Airflow Limitation"; p. 165-166; Antwerp-Wilrijk, Belgium.

Whipp, B.; "Physiologic Changes Following Bilateral Carotid-Body Resection in Patients with Chronic Obstructive Pulmonary Disease"; Chest; Jul. 31, 2008; p. 656-661; Issue 101; From the Department of Pysiology and Anesthesiology, UCLA School of Medicine; Northbrook, IL.

Winter, B.; "Bilateral Carotid Body Resection for Asthma and Emphysema: A New Surgical Approach Without Hypoventilation or Baroreceptor Dysfunction"; International Surgery; Jun. 1972; p. 458-466; vol. 57, No. 6; Presented at the Fourth Western Hemisphere Congress and the Congress of the United States Section of the International College of Surgeons; Los Angeles, CA.

Al-Rawi et al.; Effect of lignocaine injection in carotid sinus on baroreceptor sensitivity during carotid endarterectomy; J Vasc Surg; 39(6); pp. 1288-94; Jun. 2004.

(56) References Cited

OTHER PUBLICATIONS

Anand et al.; Management of the internal carotid artery during carotid body tumor surgery; Laryngoscope; 105; pp. 231-235; Mar. 1995.
Anderson et al. (executive committee); Carotid body resection; J. Allergy Clin. Immunol.; 78(2); pp. 273-275; Aug. 1986.
Arena et al.; Prognostic value of resting end-tidal carbon dioxide in patients with heart failure; Int J Cardiol; 109(3); pp. 351-358; May 2006.
Bencini et al.; The carotid bodies in bronchial asthma; Histopathology; 18; pp. 195-200; Mar. 1991.
Bencini, A.; Reduction of reflex bronchotropic impulses as a result of carotid body surgery; International Surgery; 54(6); pp. 415-423; Dec. 1970.
Bernstein et al.; Current status of glomectomy; (The Amer. Acad. Of Allergy, Abstracts of papers given at Ann. Meeting, Feb. 3-7, 1978, Boston MA; J. Allergy; 41(2); pp. 88-89; Feb. 1968.
Bishop, Jr. et al.; Paragangliomas of the neck; Arch Surg.; 127; pp. 1441-1445; Dec. 1992.
Braunwald et al.; Carotid sinus nerve stimulation for the treatment of intractable angina pectoris: surgical technic; Annals of Surgery; 172(5); pp. 870-876; Nov. 1976.
Braunwald et al.; Carotid sinus nerve stimulation in the treatment of angina pectoris and supraventricular tachycardia; The Western Journal of Medicine; 112(3); pp. 41-50; Mar. 1970.
Capps et al.; The late effects of bilateral carotid sinus denervation in man; J Clin Invest; 17(4); pp. 385-389; Jul. 1938.
Chang et al.; Impaired response to hypoxia after bilateral carotid body resection for treatment of bronchial asthma; Chest; 73; pp. 667-669; May 1978.
Curran et al.; Glomectomy for severe bronchial asthma. A double-blind study; Am Rev Respir Dis; 93(1); pp. 84-9; Jan. 1966.
Davidson et al.; Role of the carotid bodies in breath-holding; N Engl J Med; 290(15); pp. 819-822; Apr. 1974.
de Weerd et al.; Prevalence of asymptomatic carotid artery stenosis according to age and sex: Systematic review and metaregression analysis; Stroke; 40(4); pp. 1105-1113; Apr. 2009.
Dickinson et al.; Carotid body tumour: 30 years experience; Br. J. Surg.; 73 (1); pp. 14-16; Jan. 1986.
Fletcher, Jr. et al.; The surgical treatment of bronchial asthma by excision of the carotid body; J Christ Med Assoc India; 38; pp. 492-496; Sep. 1963.
Gain et al.; Anaesthesia for glomectomy in the asthmatic patient; Can Aneas Soc J; 11(4); pp. 417-424; Jul. 1964.
Giannoni et al.; Combined increased chemosensitiviy to hypoxia and hypercapnia as a prognosticator in heart failure; JACC; 53(21); pp. 1975-1980; May 2009.
Green, M.; Observations on glomectomized asthmatic patients; Annals of Allergy; 23(5); pp. 213-219; May 1965.
Gudovsky et al.; Surgical treatment of bronchial asthma (with translation); Khirurgiia; 7; pp. 14-18; 2002 (year of pub. sufficiently earlier than effective US filing and any foreign priority date).
Guz et al.; Peripheral chemoreceptor block in man; Respiration Physiology; 1; pp. 38-40; 1966 (year of pub. sufficiently earlier than effective US filing and any foreign priority date).
Hickey et al.; Bilateral carotid endarterectomy with attempted preservation of the carotid body function; Ann. Surg.; 175(2); pp. 268-273; Feb. 1972.
Honda et al.; Hypoxic chemosensitivity in asthmatic patients two decades.
Honda, Y.; Respiratory and circulatory activities in carotid body-resected humans; J Appl Physiol; 73(1); pp. 1-8; Jul. 1992.
Karashurov et al.; Radiofrequency electrostimulation of synocarotid for the treatment of bronchial asthma (with translation); Khirurgiia (Mosk); 12; pp. 4-6; 1999 (year of pub. sufficiently earlier than effective US filing and any foreign priority date).
Keim, W. F.; Carotid glomectomy in bronchial asthma; Archives of Otolaryngology; 79; pp. 225-228; Mar. 1964.
Kline et al.; Cervical glomectomy for bronchial asthma; Journal of the Medical Society of New Jersey; 61(5); pp. 176-178; May 1964.
Leggate, J. M.; Treatment of asthma by excision of the carotid body; Postgraduate Med. Journal; 26(292)pp. 71-77; Feb. 1950.
Lesske et al.; Hypertension caused by chronic intermittent hypoxia—influence of chemoreceptors and sympathetic nervous system; J Hypertens; 15(12); pp. 1593-1603; Dec. 1997.
Lo et al.; Anatomical variations of the common carotid artery bifurcation; Anz J. Surg.; 76(11); pp. 970-72; Nov. 2006.
Lugliani et al.; A role for the carotid body in cardiovascular control in man; Chest; 63(5); pp. 744-750; May 1973.
Lugliani et al.; Effect of bilateral carotid-body resection on ventilatory control at rest and during exercise in man; New England J Med; 285(20); pp. 1105-1111; Nov. 1971.
Lusiani et al.; Prevalence of atherosclerotic involvement of the internal carotid artery in hypertensive patients; Int J Cardiol; 17; pp. 51-56; Oct. 1987.
Lyons et al.; Anatomical variants of the cervical sympathetic chain to be considered during neck dissection; Br J Oral Maxillofac Surg; 36(3); pp. 180-182; Jun. 1998.
MacGOWAN, W.; Removal of the carotid body for asthma: A report of 19 treated patients; Dis Chest; 51(3); pp. 278-281; Mar. 1967.
Marschke et al.; Carotid-body removal in asthma; JAMA; 191(5); pg. 397; Feb. 1965.
Marshall, J.; Peripheral chemoreceptors and cardiovascular regulation; Physiological Reviews; 74(3); pp. 543-594; Jul. 1994.
Meyerson, Sheldon; A histological study of the morphology of the cervical carotid bifurcation, including descriptions of intramural neural elements (Thesis); Ohio State University; 47 pgs.; 1968 (year of pub. sufficiently earlier than effective US filing and any foreign priority date).
Myers et al.; End-tidal CO2 pressure and cardiac performance during exercise in heart failure; Med Sci Sports Exerc; 41(1); pp. 18-24; Jan. 2009.
Nadel et al.; Effect of changes in blood gas tensions and carotid sinus pressure on tracheal vol. and total lung resistance to airflow; J Physiol; 163(1); pp. 13-33; Aug. 1962.
Nakayama, K.; Surgical removal of the carotid body for bronchial asthma; Chest; 40(6); pp. 595-604; Dec. 1961.
Nakayama, K.; Surgical removal of the carotid body for bronchial asthma; the Australian and the New Zealand Journal of Surgery; 31(3); pp. 214-221; Feb. 1962.
Nakayama, K.; The surgical significance of the carotid body in relation to bronchial asthma; Thoracic Surgery; Journal of the International College of Surgeons; 39(4); pp. 374-389; Apr. 1963.
O'Rourke et al.; Removal of the carotid body for asthma: A preliminary report of 40 cases; The Medical Journal of Australia; 2; pp. 1040-1043; Dec. 1963.
O'Rourke et al.; Removal of the carotid body for asthma: An appraisal of results; The Medical Journal of Australia; 2; pp. 869-870; Nov. 1964.
Overholt et al.; Hidden or unsuspected brochiectasis in the asthmatic patient; JAMA; 150(5); pp. 438-441; Oct. 1952.
Overholt, R.; Glomectomy for asthma; Chest; 40; pp. 605-610; Dec. 1961.
Paliwoda et al.; Surgical removal of the carotid body and denervation of the carotid sinus for bronchial asthma; East African Medical Journal; 44(7); pp. 285-287; Jul. 1967.
Perret et al.; High prevalence of peripheral atherosclerosis in a rapidly developing country; Atherosclerosis; 153(1); pp. 9-21; Nov. 2000.
Phillips et al.; Results of glomectomy in chronic obstructive pulmonary disease: A four year follow-up report of 57 cases; Chest; 58(4); pp. 358-362; Oct. 1970.
Phillips, J.; Removal of the carotid body for asthma and emphysema; Southern Medical Journal; 57; pp. 1278-1281; Nov. 1964.
Phillips, J.; Treatment of obstructive bronchial diseases; Geriatrics; 21(7); pp. 137-143; Jul. 1966.
Ponikowski et al.; Peripheral chemoreceptor hypersensitivity; Circulation; 101; pp. 544-549; Jul. 2001.
Rabl et al.; Diagnosis and treatment of carotid body tumors; Thorac Cardiovasc Surg.; 41(6); pp. 340-343; Dec. 1993.
Sanghvi et al.; Carotid body tumors; Journal of Surgical Oncology; 54(3); pp. 190-192; Nov. 1993.

(56) References Cited

OTHER PUBLICATIONS

Sedwitz et al.; Unilateral excision of the carotid body in the treatment of 500 asthma patients; Vascular Diseases; 2; pp. 91-98; Mar. 1965.
Sedwitz, J.; Unilateral carotid body resectin for asthma; Jounal of the National Medical Association; 55(5); pp. 384-388; Sep. 1963.
Segal et al.; Glomectomy in the treatment of chronic bronchial asthma; Nejm; 272(2); pp. 57-63; Jan. 1965.
Segal, M.; Glomectomy for chronic bronchial asthma: a three phase study; Annals of Allergy; 23; pp. 377-384; Aug. 1965.
Shalev, Alon; U.S. Prov. Pat. App. No. 61/178,049 entitled "Endovascular systems for performing interventions during ischemic conditions of the CNS by utilizing the carotid baroreceptors and chemoreceptors and methods for using same," filed May 14, 2009.
Shamblin et al.; Carotid Body Tumor; Am J Surg; 122; pp. 732-739; Dec. 1971.
Shek, J.; Excision of carotid body for advanced emphysema; Michigan State Medical Society Journal; 63; pp. 211-212; Mar. 1964.
Stickland et al.; Distribution during exercise in health and chronic heart failure; Circ Res; 100; pp. 1371-1378; May 2007.
Streian et al.; Glomectomy in carotid sinus syncope and associated arrythmias: Symptomatic bradycardia, atrial flutter and atrial fibrillation; Rom J Intern Med; 44(2); pp. 153-163; 2006 (year of pub. sufficiently earlier than effective US filing and any foreign priority date).
Streian et al.; Glomectomy in carotid sinus syncope; Rev. Roum. Med.-Med. Int.; 26(1); pp. 47-52; Jan-Mar. 1988.
Tamura et al.; A morphometric study of the carotid sinus nerve in patients with diabetes mellitus and chronic alchoholism; Journal of the Autonomic Nervous System; 23; pp. 9-15; Jun. 1988.
Tchibukmacher, N.; Surgical anatomy of carotid sinus nerve and intercarotid ganglion; Surgery, Gynecology and Obstetrics; 67; pp. 740-745; 1938 (year of pub. sufficiently earlier than effective US filing and any foreign priority date).
Timmers et al.; Denervation of carotid baro- and chemoreceptors in humans; J Physiol; 553(1); pp. 3-11; Nov. 2003.
Toorop et al.; Anatomy of the carotid sinus nerve and surgical implications in carotid sinus syndrome; J Vasc Surg; 50; pp. 177-182; Jul. 2009.
Tubbs et al.; Anatomic landmarks for nerves of the neck: a vade mecum for neurosurgeons; Operative Neurosurgery; 56(ONS Suppl 2); pp. ONS256-ONS260; Apr. 2005.
Van Der Mey et al.; Management of carotid body tumors; Otolaryngol Clin North Am.; 34(5); pp. 907-924; Oct. 2001.

Ward et al.; Embolization: An adjunctive measure for removal of carotid body tumors; Laryngoscope; 98; pp. 1287-1291; Dec. 1988.
Wasserman et al.; Effect of carotid body resection on ventilatory and acid-base control during exercise; Journal of Applied Physiology; 39(3); pp. 354-358; Aug. 1975.
Wasserman et al.; Ventilation during exercise in chronic heart failure; Basic Res Cardiol; 91(suppl. 1); pp. 1-11; 1996(year of pub. sufficiently earlier than effective US filing date and any foreign priority date).
Whipp, B.J.; Carotid bodies and breathing in humans; Thorax; 49(11); pp. 1081-1084; Nov. 1994.
Williams et al.; Carotid body tumor; Arch Surg.; 127; pp. 963-968; Aug. 1992.
Winter et al.; Immediate effects of bilateral carotid body resection on total respiratory resistance and compliance in humans; Adv Exp Med Biol; 551; pp. 15-21; 2005 (year of pub. sufficiently earlier than effective US filing and any foreign priority date).
Winter, B.; Carotid body resection in chronic obstructive pulmonary disease; Chest; 100(3); pg. 883; Sep. 1991.
Winter, B.; Carotid body resection: Controversy-confusion-conflict; Ann thorac Surg.; 16(6); pp. 648-659; Dec. 1973.
Wood et al.; Bilateral removal of carotid bodies for asthma; thorax; 20(6); pp. 570-573; Nov. 1965.
Gelfand et al.; U.S. Appl. No. 13/852,895 entitled "Carotid Body Modulation Planning and Assessment," filed Mar. 28, 2013.
Gelfand et al.; U.S. Appl. No. 13/869,765 entitled "Endovascular Catheters and Methods for Carotid Body Ablation," filed Apr. 24, 2013.
Gelfand et al.; U.S. Appl. No. 13/933,023 entitled "Carotid Body Ablation Via Directed Energy," filed Jul. 1, 2013.
Engelman et al.; U.S. Appl. No. 13/936,121 entitled "Devices and Systems for Carotid Body Ablation," filed Jul. 5, 2013.
Leung et al.; U.S. Appl. No. 13/908,853 entitled "Methods and Devices for Cryogenic Carotid Body Ablation," filed Jun. 3, 2013.
Leung et al.; U.S. Appl. No. 13/908,995 entitled "Percutaneous Methods and Devices for Carotid Body Ablation," filed Jun. 3, 2013.
Chernomorsky; U.S. Appl. No. 14/516,312; entitled Percutaneous methods and devices for carotid body ablation,' filed Oct. 16, 2014.
Giannoni et al.; Clinical significance of chemosensitivity in chronic heart failure: influence on neurohormonal derangement, cheyne-strokes respiration and arrhythmias; Clinical Science (London); 114(7); pp. 489-497; Apr. 2008.
Pennes; Analysis of tissue and arterial blood temperatures in the resting human forearm; J. Appl. Physiol.; 1(2); pp. 93-122; Aug. 1948.

\* cited by examiner

SYSTEMS AND METHODS FOR TREATING DYSPNEA, INCLUDING VIA ELECTRICAL AFFERENT SIGNAL BLOCKING

CROSS-REFERENCE TO RELATED APPLICATION

The present application claims priority to U.S. Provisional Application 61/087,945, filed on Aug. 11, 2008 and incorporated herein by reference.

TECHNICAL FIELD

The present disclosure is directed generally to systems and methods for treating dyspnea, including via electrical signals that block or inhibit afferent neural signals from a patient's carotid bodies.

BACKGROUND

Dyspnea is the chief patient complaint in a variety of diseases of the pulmonary system. These diseases include chronic bronchitis (12.5 million US patients), emphysema (1.7 million US patients), and asthma (18 million US patients), collectively referred to as Chronic Obstructive Pulmonary Diseases, or COPD. Dyspnea is also reported by patients suffering from combinations of the foregoing diseases, and/or other pulmonary diseases, and non-pulmonary diseases (notably in heart failure). Dyspnea, while a common medical term, is actually poorly defined and ultimately subjective since it is generally the perception of difficulty breathing or difficulty catching one's breath, and more generally, an uncomfortable sensation of breathing.

The severity of pulmonary diseases can typically be measured using objective techniques, such as FEV1 (the patient's forced expiratory volume in the first second of exhalation), minute ventilation (the volume inhaled or exhaled by the patient in one minute), arterial blood gas levels (e.g., of oxygen or carbon dioxide), among others. By contrast, the patient's dyspnea experience can be simply one of difficulty breathing, ultimately leading to a reduction or elimination of physical activity due to this discomfort. That is, the patient complaint is of dyspnea and a loss of mobility or physical function, not of a decreased FEV1.

In many ways dyspnea can be analogous to the perception of pain. While an organic source of the pain may be present (a broken bone, for example), the pain itself can be a problem and may require palliative treatment. Furthermore, in the same way that an individual can suffer from chronic pain for which an organic cause is either absent or inadequate to cause the pain, some patients can suffer from severe dyspnea despite relatively normal objective measures of pulmonary performance.

The origins of dyspnea remain unclear. Studies and experience have yielded confusing and often seemingly contradictory results. Treatments for dyspnea range from supplemental oxygen therapy to sitting in front of a fan to systemic opiates. Furthermore, dyspnea can be experimentally induced by vigorous exercise, breath-holding, breathing through a restrictive mouthpiece, or breathing carbon dioxide in symptomatic pulmonary disease patients. A common, though unproven theory, is that dyspnea derives from a mismatch between outgoing motor signals to the respiratory muscles and incoming afferent information. In one example, under a give set of conditions, the brain can expect a certain pattern of ventilation and associated afferent feedback. Deviations from this pattern can cause or intensify the sensation of dyspnea.

While dyspnea is often the chief complaint of a patient, there is currently no pharmacologic agent that primarily treats dyspnea. That is, a variety of bronchodilators are used to treat asthma and other COPD, and while they demonstrably increase FEV1, their effects on dyspnea can be modest and can fall below that of clinical significance. Accordingly, there remains a need for methods and devices that effectively treat dyspnea.

DETAILED DESCRIPTION

The present disclosure is directed generally to systems and methods for treating dyspnea, including via electrical afferent signal inhibition. Specific details of several embodiments of the disclosure are described below with reference to particular implementations to provide a thorough understanding of these embodiments, but in other embodiments, the systems and methods may have different features. Several details describing structures or processes that are well-known and often associated with related systems and techniques, but that may unnecessarily obscure some significant aspects of the present disclosure, are not set forth in the following description for purposes of clarity. Moreover, although the following disclosure sets forth several embodiments of different aspects of the invention, several other embodiments can have different configurations or different components than those described in this section. As such, the disclosure may include other embodiments with additional elements, or without several of the elements described below with reference to FIGS. 1-7.

The present disclosure incorporates several documents by reference. In the event of inconsistent usages between this document and those documents so incorporated by reference, the usage in the incorporated reference(s) should be considered supplementary to that of this document. For irreconcilable inconsistencies, the usage in this document controls.

Overview

Several embodiments of the present disclosure are directed to using electrical signals to block, partially block, or otherwise inhibit afferent chemoreceptor signals in a patient suffering from dyspnea. The chemoreceptors provide signals to the patient's brain indicating a low level of oxygen or a high level of carbon dioxide in the patients' blood. Electrical signals provided in accordance with the technology described herein can interrupt the neuronal signals otherwise transmitted to the patient's brain by the patient's chemoreceptors, thus alleviating or eliminating the patient's sensation of breathlessness. As will be discussed in further detail later, this approach can have significant advantages over existing surgical techniques, which are irreversible and not adjustable. These and other advantages are described further below.

Relevant Physiology

Figure 1:
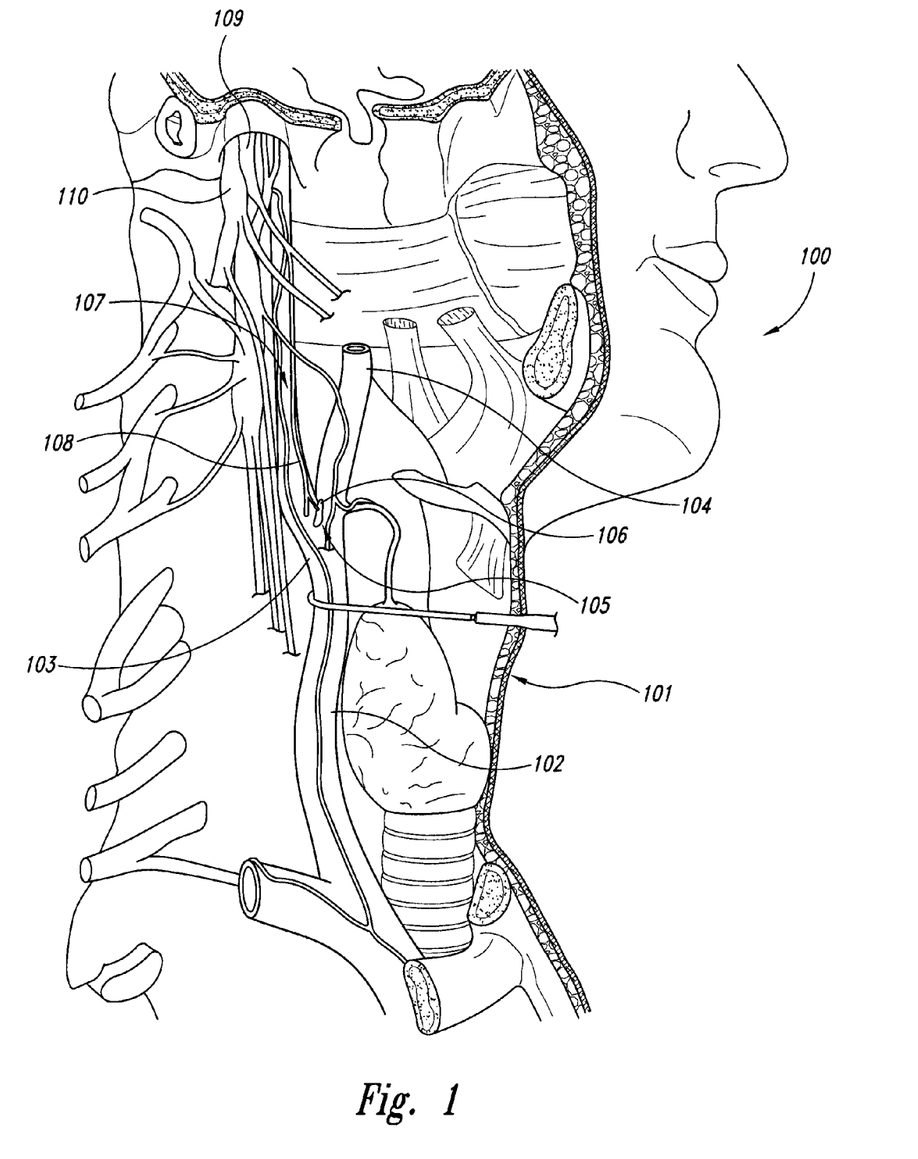
FIG. 1 is a partially cutaway, partially schematic illustration of the vascular and neural structure of a patient's neck, based on plate 124 of "Atlas of Human Anatomy", 2nd Edition, by Frank Netter (Icon Learning Systems, 2001).

FIG. 1 is a partially schematic, partially cutaway illustration of the neck region 101 of a patient 100. For purposes of clarity, many anatomical features in the neck region 101 have been eliminated in FIG. 1. FIG. 1 illustrates several relevant structures located on the right side of the patient's midline; however, the following discussion applies equally to contralateral structures located on the left side of the patient's midline. As will also be discussed further below, certain procedures may be conducted unilaterally (on either the left or right structure) or bilaterally (on both the left and right structures).

As shown in FIG. 1, the common carotid artery 102 supplies blood to the patient's head, and splits to form the internal carotid artery 103 and the external carotid artery 104 in the neck region 101. The carotid sinus 105 is located in the region of the split between the internal carotid artery 103 and the external carotid artery 104. The carotid body 106 is a small sensory organ located high in the neck region 101, posterior to the patient's lower jaw and generally in the bifurcation region between the internal carotid artery 103 and the external carotid artery 104. The carotid body 106 is perfused by blood flow in the carotid arteries 102-104. The carotid body 106 generally includes peripheral chemoreceptors that can sense the oxygen level, carbon dioxide level, and possibly pH or other factors in the arterial blood flow. These chemoreceptors provide the large majority of the patient's ability to sense oxygen, and also provide approximately one-third of the patient's ability to sense carbon dioxide. Other chemoreceptors are included at the aortic body, and in the medulla of the patient's brain. Chemoreceptors in the medulla provide approximately two-thirds of the patient's ability to sense carbon dioxide.

Afferent signals travel from the carotid body 106 to the patient's brain via the carotid branch 108 of the patient's glossopharyngeal nerve 109. The glossopharyngeal nerve 109 is the ninth cranial nerve, and descends alongside the vagus nerve or tenth cranial nerve 110. For purposes of simplicity, other cranial nerves are not specifically identified in FIG. 1. The carotid body 106, the carotid branch 108, and the glossopharyngeal nerve 109 form an afferent neural pathway 107 along which afferent signals from the chemoreceptors of the carotid body 106 are transmitted to the patient's brain.

While the exact roles and interrelationships of the various chemoreceptors remain unknown, it is commonly accepted that they can react to low levels of oxygen or high levels of carbon dioxide, and can send afferent signals to the central respiratory center that can increase the patient's ventilatory drive in order to normalize the concentration of blood gases. Conversely, removing or debilitating the carotid body 106 can render it less able to support the body's response to changing levels of blood gases by eliminating an input to the central respiratory center. In certain examples, a complete lack of response to low oxygen levels (hypoxia) or high levels of carbon dioxide (hypercapnia) can be life threatening.

Carotid Body Resection

A rare genetic mutation (often in Dutch patients) results in glomus cell tumors of the carotid body, requiring their removal via Carotid Body Resection or CBR. In some patients, bilateral tumors have required the removal of both carotid bodies. These patients typically exhibit increased exercise capacity, decreased dyspnea, increased breath-holding capacity, and a blunted ventilatory response to exercise. However, there is also evidence that these effects may be transitory and that the body may accommodate to the loss of the carotid bodies after some period of time.

Despite its current use for tumor resection, intentional CBR to treat pulmonary conditions is not currently in favor. Generally, CBR was used from the 1940's to the 1980's to treat dyspnea, including in asthmatic patients. The current disfavor derives from uncertainties about proper patient selection criteria, from concerns about inducing central sleep apnea, from possibly detrimental blood gas changes, and from the radical and irreversible nature of the surgery. Much of the disfavor derives from the history of treating asthmatic children, whose lack of response to hypoxia led them to delay treatment of acute status asthmaticus, resulting in several deaths.

Despite the foregoing drawbacks, CBR has also been associated with a significant decrease in dyspnea and a corresponding increase in exercise capacity. While blood gases are impacted, most authors appear to judge these changes to be relatively minor in many or most cases. For example, typical sequela to the chronic loss of carotid body function (in patients presumably not suffering from pulmonary disease) is a modest 6 mm Hg rise in $PaCO_2$, where "$PaCO_2$" refers to the partial pressure of carbon dioxide in the patient's arterial blood. In certain examples, patients selected for CBR have $PaCO_2$<45 mm Hg and $PaO_2$>65 mm Hg (where "$PaO_2$" refers to the partial pressure of oxygen in the patients' arterial blood), in order to ensure only a modest impact. In certain examples, many patients can have either improvements or minimal degradations in blood gases.

The literature and experience are mixed regarding the permanence of the effect of CBR. In certain examples, the effect of CBR decreases over time as the body compensates for the loss of signaling from the carotid bodies. In other examples, after CBR, other chemoreceptors can increase their responsiveness to carbon dioxide, raising the total body response back to normal levels, while having little to no compensatory change in the body's response to oxygen levels.

Inhibitory Electrical Stimulation

Aspects of the present disclosure are directed to replacing, in whole or in part, the foregoing resection procedure with an electrical stimulator implant procedure. The implanted stimulator can apply an inhibitory electrical signal to the afferent neural pathway 107, thus emulating at least in part the results of carotid body resection, but with additional control over the chemoreceptor inhibition and/or without several of the foregoing drawbacks.

Figure 2:
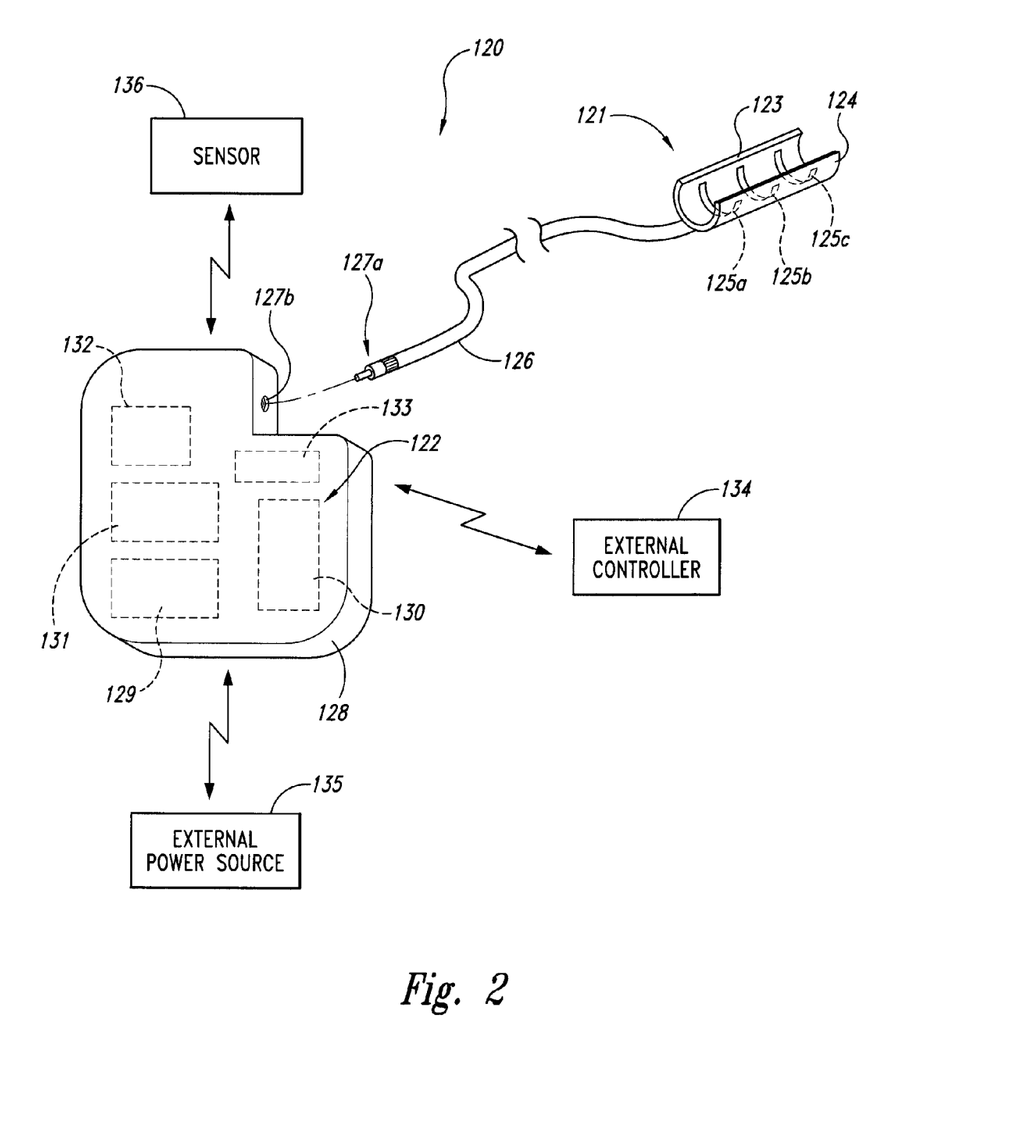
FIG. 2 is a partially schematic illustration of a system for delivering inhibitory signals to a patient's afferent chemoreceptor neural pathways in accordance with an embodiment of the disclosure.

FIG. 2 is a partially schematic, isometric illustration of a system 120 suitable for delivering inhibitory electrical signals to the afferent neural pathway 107 described above with reference to FIG. 1. Accordingly, by blocking, at least partially blocking, and/or otherwise inhibiting afferent neural signals from the chemoreceptors at the carotid body 106 (FIG. 1), the patient's dyspneic symptoms can be reduced, alleviated and/or eliminated. As described further below, this can be done without unduly interfering with the body's ability to detect and respond to low blood oxygen levels and/or high blood carbon dioxide levels.

As shown in FIG. 2, the system 120 can include a signal delivery device 121 coupled to a controller 122 with a communication link 126. In one aspect of this embodiment, the signal delivery device 121 can include a cuff electrode 123 that in turn includes a cuff or other support body 124 carrying one or more arcuate electrical contacts 125 (three are shown in FIG. 2 as first, second, and third electrical contacts 125a, 125b, 125c). In this embodiment, the cuff electrode 123 can have a tripolar arrangement, with the first and third contacts 125a, 125c connected to an anodic potential, and the second contact 125b connected to a cathodic potential. Accordingly, the outer anodic contacts 125a, 125c can direct the field lines emanating from the central cathodic contact 125b to a target neural population. In other embodiments, the cuff electrode 123 can include other arrangements of contacts, e.g., to provide monopolar or bipolar signals. In any of these embodiments, the cuff electrode 123 can be positioned around or adjacent to any suitable portion of the afferent neural pathway 107 (FIG. 1), including the carotid body 106 itself and/or the carotid branch 108. The particular location at which the cuff electrode 123 is placed can be selected based on factors including an individual patient's physiology, characteristic chemoreceptor responsiveness and/or characteristic baroreceptor responsiveness.

The signal delivery device 121 is coupled to the controller 122 via a communication link 126 having a first connector 127a that may be releasably engaged with a second connector 127b. The second connector 127b is electrically coupled to the controller 122, and both the second connector 127b and the controller 122 can be carried by an enclosed, hermetically sealed housing 128. The housing 128 can also enclose an internal power source 129 which provides power to a pulse generator 130. The pulse generator 130 generates pulses (e.g., square wave, biphasic, charge-balanced and/or other suitable pulses) that are transmitted to the signal delivery device 121 via the communication link 126, under the direction of the controller 122. The controller 122 can accordingly include a memory 131, a processor 132, and a receiver/transmitter 133. Instructions for delivering the electrical signal to the patient via the signal delivery device 121 can be stored in or on one or more computer readable media of the controller 122, e.g., the memory 131 and/or the processor 132. Accordingly, the controller 122 can include a specially programmed computer device.

In a particular embodiment, the receiver/transmitter 133 can receive inputs from devices within or outside the housing 128 to operate in an open loop manner and/or a closed loop manner. For example, the system 120 can include an external controller 134 that communicates instructions to the receiver/transmitter 133 via a wireless link. A physician can use an external controller 134 to change the instructions carried out by the controller 122. In another embodiment, the patient can use an external controller 134 to start and/or stop the signals directed by the controller 122 to the signal delivery device 121. The physician and the patient can each have separate external controllers 134, with the physician's external controller 134 able to carry out a broader range of control tasks than the patient's external controller 134. This arrangement can prevent the patient from inadvertently changing signal delivery parameters in an undesirable manner, while still allowing the patient to control certain tasks e.g., starting and stopping the electrical signals.

The receiver/transmitter 133 can also receive information from one or more sensors 136. The sensors 136 can be configured and positioned to provide information to the controller 122 useful for determining when and in what manner to provide electrical signals to the signal delivery device 121. For example, the sensor 136 can include an oxygen sensor (e.g., an implanted oxygen sensor, or an external fingertip-mounted oxygen sensor) that identifies the patient's blood oxygen levels. In another embodiment, the sensor 136 can include an accelerometer or other device that detects the patient's activity level. In still another embodiment, the sensor 136 can include a clock or timer that senses the passage of time, which, as described further below, may also be used to control the manner in which electrical signals are delivered to the patient.

As shown in FIG. 2, the internal power source 129 can be included in the implantable housing 128. The housing 128 can be implanted at a subclavicular location in the patient's chest, or at another suitable location. In a particular embodiment (e.g., when the internal power source 129 includes a rechargeable battery), the system 120 can include an external power source 135 that is used to recharge the internal power source 129 within the implanted housing 128. For example, the external power source 135 can recharge the internal power source 129 via inductive coupling. In another embodiment, the internal power source 129 can be eliminated, and the external power source 135 alone can provide power to implanted controller 122. In still another embodiment, the controller 122 and the other components located in the housing 128 can be positioned outside the patient's body. For example, these components can be placed in an external housing and worn by the patient, e.g., beneath the patient's clothing. The controller 122 can be connected to the signal delivery device 121 via a hardwired transdermal communication link, or via a wireless transcutaneous link. Any one or combination of the foregoing arrangements can be used to transmit suitable electrical signals to the signal delivery device 121.

Figure 3:
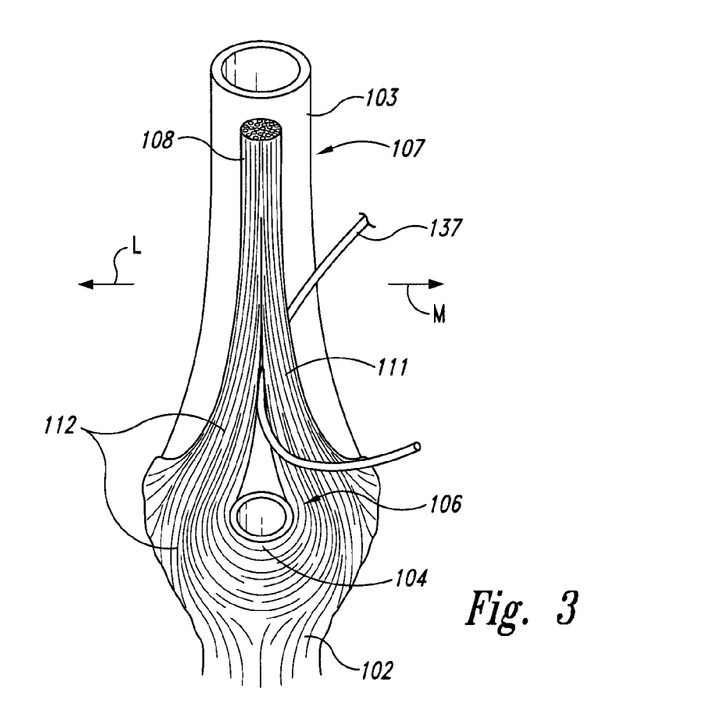
FIG. 3 is a partially schematic, generally ventral view of a patient's carotid arteries and carotid branch, based on FIG. 1 of an article titled "Bilateral Carotid Body Resection for Asthma and Emphysema" (Winter, *International Surgery*, Volume 57, No. 6, June 1972, hereinafter "Winter").

FIG. 3 is a partially schematic, ventral illustration of a portion of the anatomy shown in FIG. 1, illustrating a technique for implanting a signal delivery device in accordance with an embodiment of the disclosure. Certain aspects of this technique are generally similar to those disclosed by Winter in an article titled "Bilateral Carotid Body Resection for Asthma and Emphysema," (*International Surgery*, Volume 7, No. 6, June 1972, hereinafter "Winter"), incorporated herein by reference. FIG. 3 illustrates the region at which the common carotid artery 102 bifurcates into the internal carotid artery 103 and the external carotid artery 104. Arrows M and L identify medial and lateral directions, respectively. Most of the external carotid artery 104 has been cut away so as to illustrate the carotid branch 108 located between the internal carotid artery 103 and the external carotid artery 104. The carotid branch 108 includes baroreceptor neurons 112 and chemoreceptor neurons 111 that extend to the carotid sinus 104 and the carotid body 106 to transmit afferent neural signals from the patient's baroreceptors and chemoreceptors, respectively. In a particular embodiment of the method disclosed herein, a probe 137 or other surgical implement can be used to separate or divide the chemoreceptor neurons 111 from the baroreceptor neurons 112, thus allowing a representative signal delivery device 121 (FIG. 2) to be positioned in a manner that preferentially directs signals to the chemoreceptor neurons 111 over the baroreceptor neurons 112. For example, the cuff electrode 123 (FIG. 2) can be positioned around the chemoreceptor neurons 111, with the electrode contacts 125a-c preferentially positioned to direct signals to the chemoreceptor neurons 111 over the baroreceptor neurons 112. While some electrical signals may still reach the baroreceptor neurons 112, this arrangement can more significantly inhibit or block afferent signals transmitted along the chemoreceptor neurons 111, without unduly interfering with afferent signals transmitted by the baroreceptor neurons 112.

Figure 4:
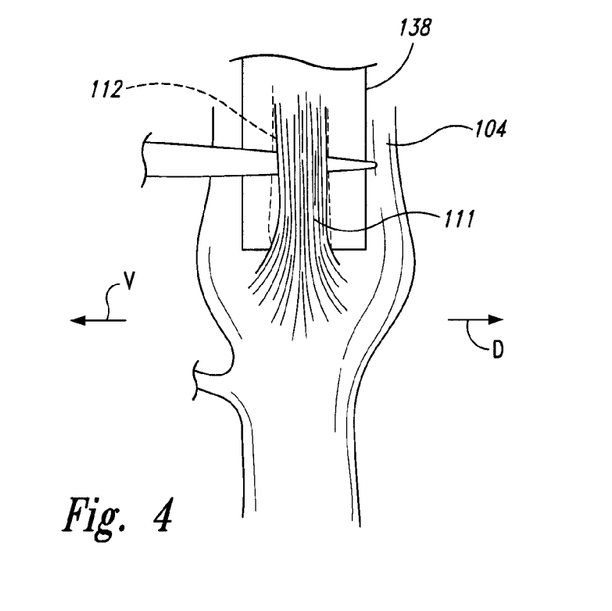
FIG. 4 is a partially schematic lateral view of the patient's carotid artery region, based on FIG. 4 of Winter.

FIG. 4 is a partially schematic, left lateral view of the anatomy shown in FIG. 3, also based on Winter, and illustrating the chemoreceptor neurons 111 after having been divided from the baroreceptor neurons 112. Arrows D and V identify dorsal and ventral directions, respectively. As discussed above, a suitable signal delivery device 121 (FIG. 2) can be positioned so as to preferentially direct electrical signals to the chemoreceptor neurons 111. In at least some embodiments, the characteristics of the signal delivery device 121 itself and the orientation of the signal delivery device 121 will preferentially direct signals to the chemoreceptor neurons 111. In other embodiments, the physician can implant an insulating shield 138 between the chemoreceptor neurons 111 and the baroreceptor neurons 112 so as to restrict or prevent electrical signals directed to the chemoreceptor neurons 111 from unduly affecting the baroreceptor neurons 112, and/or other nearby or neighboring structures. The shield 138 can be held in place with a suitable adhesive, suitable friction features (e.g., nubs) and/or other arrangements.

Figure 5:
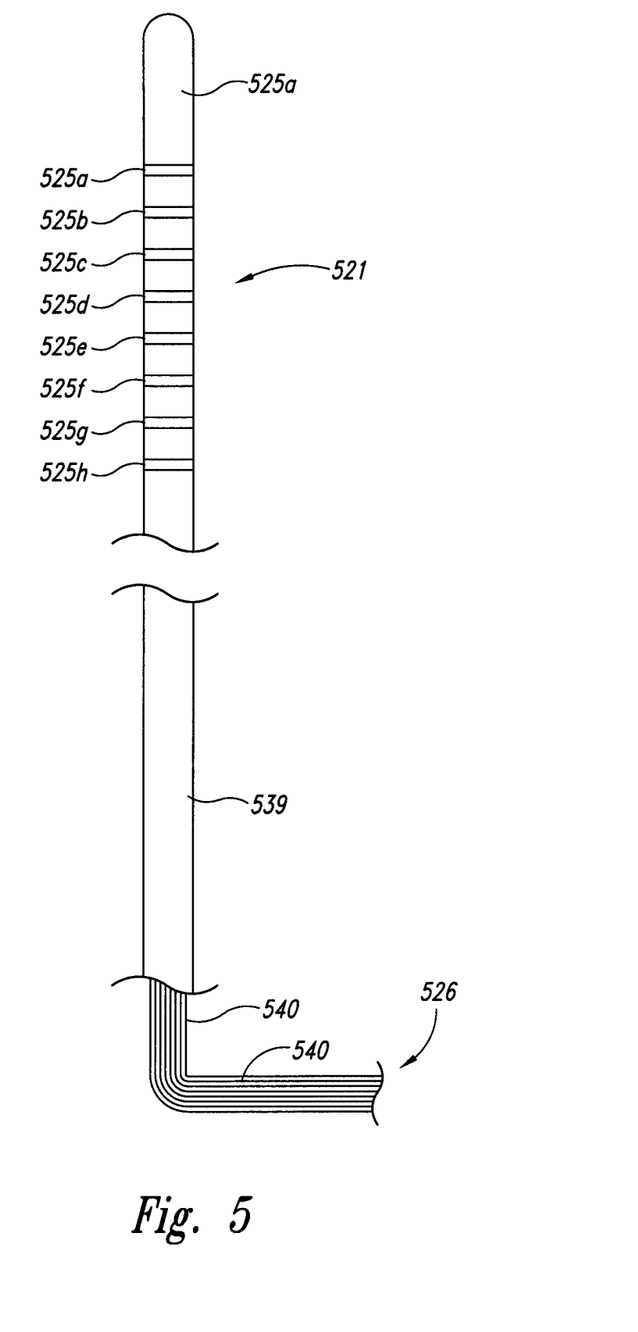
FIG. 5 is a partially schematic illustration of a lead suitable for providing signals in accordance with an embodiment of the disclosure.

The signal delivery device 121 positioned in signal communication with the chemoreceptor neurons 111 can have an arrangement generally similar to that shown in FIG. 2, or in other embodiments, it can have other arrangements. For example, FIG. 5 illustrates a signal delivery device 521 that includes a lead 539 typically used for spinal cord stimulation. The lead 539 can carry a plurality of electrical contacts 525 (eight are shown in FIG. 5 as contacts 525a, 525b . . . 525h). Each of the contacts 525 can have an annular ring shape with an outer surface exposed at the outer surface of the lead 539. Each contact 525 can be connected to an individual electrical conductor 540 (e.g., a wire) so as to receive a separately programmable electrical signal. The individual conductors 540 can form a communication link 526 via which the contacts 525 are connected to the controller 122 (FIG. 2). The individual contacts 525a-525h can be selectively activated to provide suitable inhibitory signals, without unnecessarily stimulating adjacent structures. Individual active contacts may selectively be activated or deactivated to avoid habituation and/or tissue necrosis. The lead 539 can be delivered percutaneously and positioned alongside the chemoreceptor neurons 111 shown in FIG. 4, and can be secured in place using suitable sutures or other securement techniques.

In one embodiment, the practitioner (e.g., a surgeon or other physician) can apply the dividing technique and the signal delivery device implanting technique described above to both left and right carotid branches. Accordingly, the practitioner can implant two bilaterally positioned signal delivery devices, coupled to a common implanted or externally-worn controller. In another embodiment, the chemoreceptor neurons and/or the carotid body on one side of the patient's midline can be resected, ligated or otherwise surgically disabled, and the contralateral structures can receive inhibitory signals from an implanted electrical signal delivery element. In a further aspect of this embodiment, the resection process can include resecting both the chemoreceptor neurons and the baroreceptor neurons by resecting the carotid branch 108 or the carotid body 106. Due to the body's other still-active baroreceptors, the effect of this procedure on the body's overall baroreceptor functioning is not expected to be significant for at least some classes of patients. Due to the combination of surgically disabling chemoreceptor pathways on one side of the patient's body, and applying inhibitory electrical stimulation to the chemoreceptor pathways on the opposite side of the patient's body, the patient's dyspneic effects can be controlled.

The process of resecting one chemoreceptor pathway (and optionally one baroreceptor pathway) may be advantageous because it can simplify the surgical procedure, and/or it can conserve battery power. For example, it may be simpler for the practitioner to implant a signal delivery device at the patient's right side chemoreceptor pathway and then resect the patient's left side chemoreceptor pathway than it is for the practitioner to implant a second signal delivery device and tunnel the associated communication link to an implanted controller. In addition, one signal delivery device is expected to consume less power than two. Conversely, some patients may benefit from the ability to reactivate and/or modulate chemoreceptor functioning on both sides of the midline. In such cases, the practitioner may implant bilateral signal delivery devices, as discussed above, rather than surgically disable one chemoreceptor afferent neural pathway.

Figure 6:
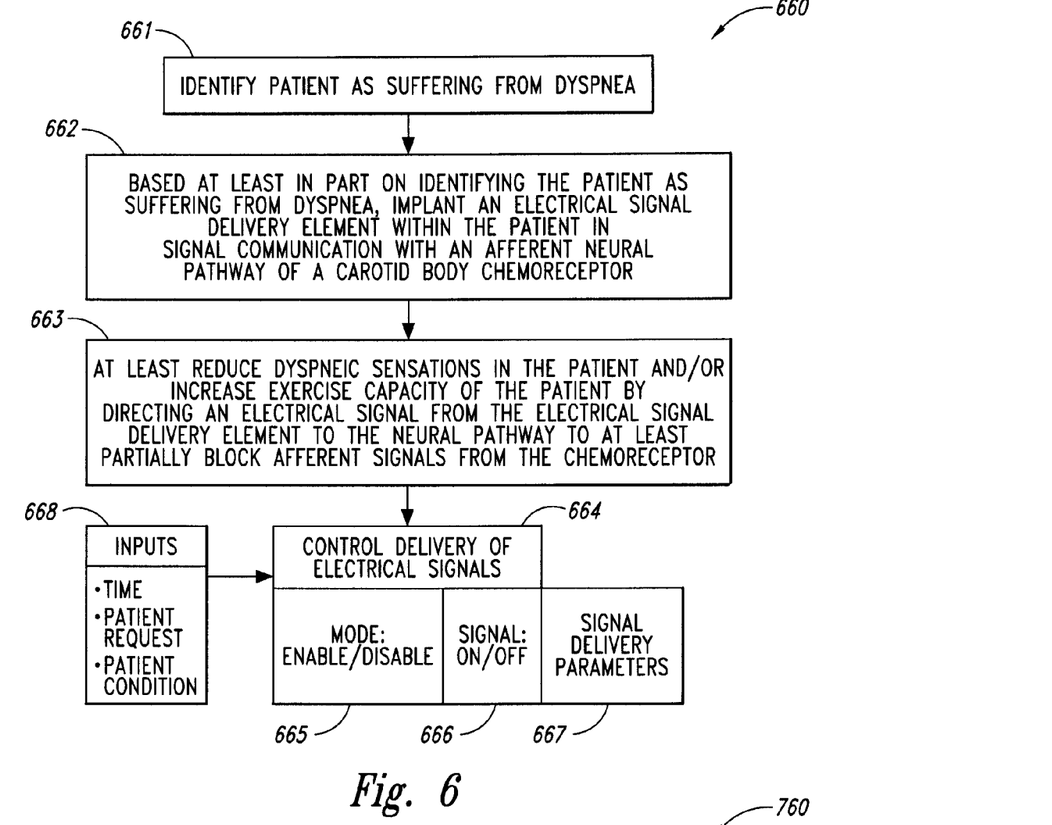
FIG. 6 is a block diagram illustrating a method for treating a patient in accordance with an embodiment of the disclosure.

FIG. 6 is a block diagram illustrating a process or method 660 for treating a patient in accordance with a particular embodiment of the present disclosure. The process 660 includes identifying a patient as suffering from dyspnea (process portion 661). The process 660 can further include implanting an electrical signal delivery element within the patient to be in signal communication with an afferent neural pathway of a carotid body chemoreceptor, based at least in part on identifying the patient as suffering from dyspnea (process portion 662). Accordingly, the process 600 can include deliberately tying a diagnosis of dyspnea to treatment of dyspneic symptoms via specifically directed inhibitory electrical signals provided by an electrical signal delivery element in signal communication with target neurons of the afferent neural pathway. As used in this context, signal communication means that electrical signals emanating from the electrical signal delivery element have a direct effect on the afferent neural pathway by virtue of interactions between the electrical signal and the neurons of the afferent neural pathway. For example, the electrical signal delivery element can include one or more electrical contacts positioned along the carotid branch 108 of the glossopharyngeal nerve 109 (FIG. 1). In particular embodiments, the electrical contacts can be positioned at or up to about five centimeters superior to the carotid body 106. The electrical contacts can be in physical contact with the adjacent neural tissue, or otherwise close enough to the neural tissue to have the desired inhibitory effect on the afferent signals. The contacts can accordingly be positioned to preferentially direct signals to the chemoreceptor neurons, as described above with reference to FIGS. 4 and 5.

The process 660 can further include at least reducing dyspneic sensations in the patient and/or increasing the patient's capacity for exercise by directing an electrical signal from the electrical signal delivery element to the neural pathway to at least partially block afferent signals from the chemoreceptor (process portion 663). For example, the electrical signal delivery element can direct biphasic, square wave, charge-balanced pulses at a frequency from about 1,000 Hz to about 10,000 Hz, an amplitude of up to about 12 volts or up to about 10 milliamps, with individual pulses having a duration of from about 10 microseconds to about 1,000 microseconds. In a particular embodiment, the frequency is selected to be about 5,000 Hz, the pulse width is selected to be 30-50 microseconds, and the amplitude is selected to be from about 1 mA to about 5 mA, with the selected value chosen to avoid muscle capture. In a particular embodiment, the pulses can be applied unilaterally to the afferent neural pathway associated with either the left side or right side carotid body. In a particular aspect of this embodiment, the signals can be provided in a burst lasting about 120 seconds. The resulting block or partial block provided by the applied signals can have a persistence (e.g., an effective duration after the end of the burst) that lasts for approximately 90 to 120 seconds. The signal can be applied with a duty cycle of about 50% in a particular embodiment, or other suitable values selected to provide efficacy while conserving power in other embodiments. The level of efficacy can be based at least in part on the persistence effect of the signal.

In another embodiment, the stimulation can be provided bilaterally, via one signal delivery device positioned along one afferent neural pathway, and another signal delivery device positioned along the contralateral afferent neural pathway. Each of the signal delivery devices can be connected to a common controller. In this arrangement, delivering bilateral electrical signals can produce the desired inhibitory effect on afferent signals transmitted from the chemoreceptors that lasts for hours rather than minutes.

The process 660 can further include controlling the delivery of the electrical signals provided to the signal delivery element (process portion 664). The signals can be controlled in a manner that is responsive to one or more inputs 668. In a particular embodiment, the electrical signals can be controlled in part by alternating between an enable mode and a disable mode (process portion 665). In the enable mode, signals may be selectively turned on and off (process portion 666) via a separate instruction. The signals are the delivered in accordance with suitable signal delivery parameters 667, including the frequencies, amplitudes and pulse widths described above. In the disable mode, signals may not be selectively turned on or off, despite the separate instruction. For example, the system can enter the enable mode during normal waking hours, allowing the patient to activate the signal delivery element on an as-needed basis via a separate, patient-directed input. During normal sleeping hours, the system can enter the disable mode, during which the system will not direct electrical signals, even if concurrently requested by the patient. This arrangement can prevent the patient from inadvertently inhibiting the carotid body chemoreceptors at night, so as to reduce or eliminate the possibility of inducing sleep apnea. During waking hours, with the system in the enable mode, the patient can selectively inhibit chemoreceptor afferent signals, for example, before and/or during exercise, by providing a separate instruction. The instruction can be provided when the patient presses a button or otherwise enters an input signal via the external patient controller 134 described above with reference to FIG. 2.

The foregoing example is representative of one in which the system responds to a time input (e.g. normal waking hours and normal sleeping hours) and a patient request (e.g. a specific request for inhibitory electrical signals). In other embodiments, the system can respond to other time-based and/or patient-based inputs. For example, the system can remain on (e.g. actively delivering signals to the signal delivery element) for a period of 30 minutes or another suitable period, in response to receiving a patient request. The patient request can come in the form of an input from a simple electronic device (e.g., the patient controller 134 described above with reference to FIG. 2), or a magnet that activates a reed switch. The patient request can arrive in anticipation of carrying out an activity (e.g. exercise), and/or can be provided during an activity. Accordingly, the system can automatically provide for a maximum active signal time per patient-initiated or otherwise-initiated activation. In another embodiment, the system can automatically provide for a minimum inactive time or off time between patient or otherwise initiated activations. In still a further embodiment, the system can automatically track a maximum amount of signal delivery time per suitable time interval. For example, the system can track a maximum number of hours of active signal time per day. If the patient requests more than this amount of time, the system can prevent further activations, or require a particular activation sequence or physician intervention before authorizing additional activations. Representative suitable activation times per day include 1, 2, 4, 6 or 8 hours.

In still further embodiments, process portion 664 can include receiving inputs relating to patient state or condition. For example, the system can deliver or enable delivery of the electrical signals in response to an indication that the patient is physically active (a first state or condition), and disable or cease delivering the signals when the patient is resting or relaxing (a second state or condition). In a particular example, an accelerometer or other motion detection device can provide suitable inputs for this mode of operation. In another embodiment, an electrocardiogram can provide a generally similar function by providing an indication of the patient's heart rate. In still further embodiments, indications of the patient's condition can be used to provide alerts and/or to prevent the inhibitory signals from being directed to the chemoreceptors. For example, the input can include an indication of the patient's blood oxygen level, and can prevent the system from delivering electrical signals if the blood oxygen level is below a particular threshold. In representative embodiments, the system can deliver signals when the blood oxygen level is at or above a first threshold of 89%, 90%, 91%, 92% or 93%, and can cease delivering signals when the blood oxygen level is at or below a second threshold of 93%, 92%, 91%, 90% or 89%. In other embodiments, these values can be based on partial pressures (e.g., 60, 65 or 70 mm $PaO_2$). In still further embodiments, the foregoing activation determination can be based on blood carbon dioxide levels (e.g., less than 35, 40, 45 or 50 mm $PaCO_2$). The foregoing actions can be accompanied by an alarm function, or the alarm function can be provided without the automatic shutdown feature, but with the patient taking the separate step of shutting the system down. This arrangement can make use of an external or internal pulse-oxymeter, such as a light-sensitive oxymeter worn on the patient's fingertip.

In other embodiments, the detector can detect breathing motion and/or other pulmonary indicators. Any of the foregoing detection techniques can be used to monitor the patient, alert the patient, and/or automatically or manually shut the system off or otherwise disable or deactivate the system, while the patient is awake and inactive, while the patient is awake and active, or while the patient is asleep. In any of these embodiments, the system can be subsequently reactivated or enabled, e.g. by a physician or other practioner, or by the patient.

Figure 7:
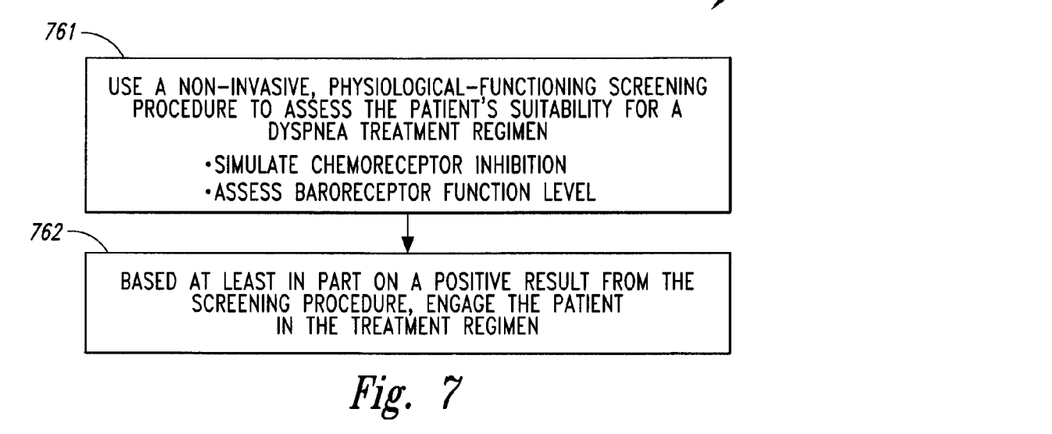
FIG. 7 is a block diagram illustrating a method for diagnosing and treating a patient in accordance with another embodiment of the disclosure.

FIG. 7 is a block diagram illustrating a method 760 that includes diagnosing and/or screening patients in accordance with a particular embodiment of the disclosure. In general, the foregoing procedures for treating dyspnea may be applied to patients with severe or very severe COPD, as evidenced by FEVI values of between about 20% and about 40%. Such patients may also demonstrate exercise limited by dyspnea (e.g. a value of 3-4 on the MRC 1-5 point scale). Such patients may have similar blood chemistries to those selected for CBR, e.g., $PaCO_2<45$ mm Hg and $PaO_2>65$ mm Hg.

Process portion 761 includes using a non-invasive, physiological-functioning screening procedure to assess the patient's suitability for a dyspnea treatment regimen. This process can include, for example, simulating chemoreceptor inhibition to determine or estimate the likelihood that the patient will respond to the subsequent inhibition provided by an implanted signal delivery device and/or resection. The process can, in addition to or in lieu of the foregoing screen, include assessing the patient's baroreceptor functioning level, which can be used to aid the physician in determining whether some of the patient's baroreceptor functions can be reduced or eliminated in combination with inhibiting chemoreceptor functions. Each of these assessments is described in turn below.

The practitioner can employ one or more of several techniques for reversibly simulating the effects of chemoreceptor inhibition before undertaking a resection or implant procedure. For example, the patient can receive a locally injected anesthetic applied to the carotid bodies during or before an exercise test to determine the impact of carotid body blocking on exercise capacity and/or perceived dyspnea. The dyspneic relief and/or increase in exercise capacity can be compared to the impact on the patient's blood gasses to determine a suitable treatment. For example, if the patient reports a positive effect on the dyspneic symptoms and/or an increased capacity for exercise, and results indicate an acceptable effect on the patient's blood gasses (e.g. an acceptable reduction in blood oxygen), the patient may be identified as a suitable candidate for further treatment. A representative acceptable reduction in blood oxygen level is about 6 mm Hg $PaO_2$, or less.

In another example, the carotid body's output can be artificially suppressed by the inhalation of high fraction oxygen (a gas mixture of greater than approximately 30% oxygen). Aspects of a representative process carried out on COPD patients are described by Somfay et al. in "Dose-reponse effect of oxygen on hyperinflation and exercise endurance in nonhypoxaemic COPD patients" (European Respiratory Journal, vol. 18, 77-88, 2001, incorporated herein by reference). These individuals exhibited significantly increased exercise capacity due to the elimination of carotid body nervous signaling. Accordingly, breathing such a hyperoxic gas mixture can be used both to quantify the magnitude of the effect of inhibitory electrical stimulation or combined electrical stimulation and resection. Suitable levels of oxygen for the foregoing screening procedure include at least 30%, at least 40%, at least 50% and about 100%.

Another aspect of process portion 761 is assessing the patient's baroreceptor functioning level. For example, known reversible techniques such as carotid sinus massage or intraoperative anesthetic applied to the carotid sinus can be used to determine the functioning of the baroreceptors carried by the patient's carotid bodies. In particular, these techniques can be used to determine if disabling the carotid sinus baroreceptor function has an effect on the patient's overall barosensing function, and/or to determine the patient's sensitivity to loss of sinus cavity barosense function. If it is determined that the patient's overall baroreceptor functioning is adequate without the specific feedback provided by the carotid body baroreceptors (e.g. if other baroreceptors located in the brain or elsewhere by themselves provide a suitable functioning level at or above a selected threshold), then the practitioner can undertake procedures that may inhibit the baroreceptor functioning of the carotid bodies in addition to the chemosensing functioning of the carotid bodies. For example, when resecting the carotid body or carotid nerve, the practitioner can resect both the chemoreceptor neurons and the baroreceptor neurons if doing so will not unacceptably affect the patient's baroreceptor functioning. Similarly, the practitioner can implant the signal delivery device in a manner that may inhibit afferent signals from the carotid body baroreceptors (e.g., without preference to inhibiting only chemoreceptor neurons) if doing so is not expected to unacceptably affect the overall baroreceptor functioning of the patient. If the patient's barosense function is significantly affected by temporarily reducing or eliminating the carotid sinus barosense function, the practitioner can take appropriate steps to preferentially direct inhibitory signals to the chemoreceptor neurons to avoid unnecessarily obstructing the functioning of the baroreceptor neurons.

After the chemoreceptor and/or baroreceptor screening functions have been conducted (process portion 761), the patient may be selected for dyspnea treatment (process portion 762). The dyspnea treatment can include, for example, the techniques described above with reference to FIGS. 1-6. In other embodiments, the screening techniques shown in FIG. 7 can be used as a precursor to other dyspnea therapies.

One aspect of several of the embodiments described above is that the foregoing systems and methods can relieve the patient's dyspnea while the patient is exercising and/or engaging in other waking activities, with an expected modest degradation of blood gasses. An advantage of this arrangement is that by reducing dyspneic symptoms, the patient can be more relaxed and more likely to engage in exercise, and/or engage in exercise more often, and/or engage in more strenuous exercise, which can facilitate the patient's participation in pulmonary rehabilitation. The patient may have a brief reduction in blood oxygen (e.g. from 95% to 92%), but the short-term effect of this reduction may be more than offset by the long-term effects of increased exercise. This can halt or even reverse what has been viewed as a dyspneic spiral in which (a) the patient suffers from COPD and dyspnea, (b) the dyspnea discourages the patient from engaging in exercise, which (c) exacerbates the COPD and dyspnea. Thus, in a manner analogous to pain treatment, reducing the patient's dyspnea can allow the patient to engage in activity despite the existence of an underlying condition, and in at least some instances, to an extent that treats the underlying condition.

In addition to or in lieu of increasing the patient's level of exercise, embodiments of the foregoing systems and methods can increase the patient's level of other activities, e.g., activities of daily living. In addition to, or in lieu of the foregoing advantages, aspects of the foregoing systems and methods can improve the patient's quality of life by eliminating or reducing the patient's use of and/or reliance on supplemental oxygen, which is typically carried by the patient in a heavy, awkward tank. Eliminating or reducing the use of supplemental oxygen is expected to further increase the likelihood and/or frequency with which the patient exercises.

Another feature of several of the foregoing embodiments is that the effect of the electrical signal on the chemoreceptor afferent neural pathway is controllable and reversible. Accordingly, the signal can be halted while the patient is sleeping, resting, relaxing, or otherwise not engaged in strenuous activity. This can allow the afferent neurons to return to a normal state and, correspondingly allow the patient's blood gasses to return to normal (or at least normal for that patient) levels. In addition, if inhibiting the chemoreceptor afferent neural pathway later becomes undesirable, the system can be deactivated. The system can subsequently be reactivated if inhibiting the chemoreceptors again becomes part of a suitable therapy. This is unlike resection, which is generally irreversible.

Still another feature of at least some of the foregoing embodiments is that the system can automatically monitor and respond to changes, and can control the delivery of electrical signals accordingly. For example, the system can automatically disable electrical signal delivery during normal sleeping hours to avoid apnea. The system can automatically disable electrical signal delivery if blood gasses degrade below desired levels. This level of automation takes advantage of and builds on the fact that the effect of the electrical signals is reversible and haltable.

Still another aspect of several of the foregoing embodiments is that the system can be selectively activated and deactivated as part of an overall treatment regimen that includes exercise. For example, the system can be activated during high intensity exercise experienced during pulmonary rehabilitation or post rehabilitation maintenance. At other times, the system can be deactivated. In still a further embodiment, the degree to which the system inhibits the afferent signals from the chemoreceptors can be controlled. For example, the amplitude and/or duty cycle of the signal applied to the neural pathways can be increased for additional inhibition and decreased for less inhibition. In another approach that can be used in addition to or in lieu of the foregoing approach, the carotid body chemoreceptors on one side of the patient's midline can be inhibited while those on the other side are not. In yet a further embodiment, the system can alternate between inhibiting chemoreceptors on one side of the midline and those on the other. This arrangement can be used to forestall or prevent patient habituation to the electrical signals. In addition to or in lieu of this arrangement, the signal delivery parameters (e.g., signal amplitude, frequency, pulse width, and/or parameters) can be varied to forestall or prevent habituation. In still another embodiment, the system can be activated only at selected times (e.g., during exercise) to reduce habituation. Accordingly, the foregoing processes can extend the effectiveness of the therapy for a longer, controlled period of time.

From the foregoing, it will be appreciated that specific embodiments of the disclosure have been described herein for purposes of illustration, but that various modifications may be made without deviating from the disclosure. For example, the particular signal delivery parameters described above can have other values in other embodiments. The particular electrodes described above can have other configurations and other embodiments. The system can include sensors other than those specifically identified above. Certain aspects of the disclosure described in the context of particular embodiments may be combined or eliminated in other embodiments. For example the patient may receive an electrode device of the type shown in FIG. 2 on one side of the body, and an electrode device of the type shown in FIG. 5 on the other side. Further, while advantages associated with certain embodiments have been described herein in the context of those embodiments, other embodiments may also exhibit such advantages, and not all embodiments need necessarily exhibit such advantages to fall within the scope of the present invention. Accordingly, the disclosure can include other embodiments not explicitly shown or described above.

We claim:

1. A method for treating a patient comprising directing an electrical signal from an electrical signal delivery device to a carotid body in a human patient to block afferent signals from the carotid body,
   further comprising positioning the electrical signal delivery device with respect to the carotid body such that blocking the afferent signals from the carotid body with the electrical signal does not interfere with afferent signals transmitted by baroreceptor neurons in the patient,
   wherein the blocking of the afferent signals achieves a therapeutic effect by disabling a function of the carotid body in sensing hypoxia or hypercapnia.

2. The method of claim 1 wherein directing an electrical signal from an electrical signal delivery device to a carotid body comprises directing an electrical signal in bipolar mode.

3. The method of claim 1 further comprising, prior to directing the electrical signal, simulating carotid body inhibition.

* * * * *